(12) United States Patent
Oñativia Bravo et al.

(10) Patent No.: US 11,426,257 B2
(45) Date of Patent: Aug. 30, 2022

(54) SELF-IDENTIFYING SURGICAL CLAMP, FIDUCIAL ELEMENT FOR USE WITH SUCH A CLAMP AND KITS COMPRISING SUCH CLAMPS AND FIDUCIAL ELEMENTS

(71) Applicant: Cyber Surgery, S.L., San Sebastian (ES)

(72) Inventors: Jon Oñativia Bravo, Mendaro (ES); Jorge Presa Alonso, Mendaro (ES); Álvaro Escudero Martínez De Ibarreta, Mendaro (ES); Alfonso Urzainqui Glaria, Mendaro (ES); Álvaro Bertelsen Simonetti, Mendaro (ES)

(73) Assignee: Cyber Surgery, S.L., San Sebastian (ES)

( * ) Notice: Subject to any disclaimer, the term of this patent is extended or adjusted under 35 U.S.C. 154(b) by 137 days.

(21) Appl. No.: 16/612,700

(22) PCT Filed: May 12, 2017

(86) PCT No.: PCT/ES2017/070304
§ 371 (c)(1),
(2) Date: Nov. 11, 2019

(87) PCT Pub. No.: WO2018/206829
PCT Pub. Date: Nov. 15, 2018

(65) Prior Publication Data
US 2020/0129264 A1    Apr. 30, 2020

(51) Int. Cl.
*A61B 90/00* (2016.01)
*A61B 90/98* (2016.01)

(52) U.S. Cl.
CPC .............. *A61B 90/39* (2016.02); *A61B 90/98* (2016.02); *A61B 2090/3983* (2016.02); *A61B 2090/3991* (2016.02)

(58) Field of Classification Search
CPC .................... A61B 34/20; A61B 90/39; A61B 2017/00477; A61B 2090/3983;
(Continued)

(56) References Cited

U.S. PATENT DOCUMENTS

| 6,093,930 A | * | 7/2000 | Boyette, Jr. | ............ G01Q 70/02 250/442.11 |
| 2002/0107538 A1 | * | 8/2002 | Shibata | .......... A61B 17/320068 606/169 |

(Continued)

FOREIGN PATENT DOCUMENTS

| DE | 10 2010 037758 A1 | 3/2012 | |
| EP | 0236414 B1 * | 5/1991 | ............. G01B 7/008 |
| WO | WO 97/29709 A1 | 8/1997 | |

OTHER PUBLICATIONS

International Search Report; -PCT/ES2017/070304; dated Aug. 17, 2017; 6 pages.

*Primary Examiner* — Carolyn A Pehlke
*Assistant Examiner* — Johnathan Maynard
(74) *Attorney, Agent, or Firm* — Knobbe Martens Olson & Bear LLP

(57) ABSTRACT

A surgical clamp comprising two halves, each halve with an upper (2) and a lower portion (3), the lower portions forming two jaws (3) adapted to be in contact with a surgical site, one of the upper portions (2) being provided with a kinematic coupling mechanism (4, 5) and a passive circuit with a predetermined impedance value such that it is possible to identify different clamps because of their different impedances.

20 Claims, 5 Drawing Sheets

(58) Field of Classification Search
CPC .... A61B 2090/3991; A61B 2090/3966; G05B 2219/49296
See application file for complete search history.

(56) References Cited

U.S. PATENT DOCUMENTS

| | | | |
|---|---|---|---|
| 2005/0215888 A1 | 9/2005 | Grimm et al. | |
| 2007/0270681 A1* | 11/2007 | Phillips | A61B 90/39 600/407 |
| 2009/0024127 A1 | 1/2009 | Lechner et al. | |
| 2009/0306499 A1* | 12/2009 | Van Vorhis | A61B 34/20 606/130 |
| 2010/0312096 A1* | 12/2010 | Guttman | A61B 34/25 600/411 |
| 2010/0324580 A1* | 12/2010 | Yamada | A61B 17/320092 606/169 |
| 2011/0017801 A1* | 1/2011 | Zemlok | A61B 17/07207 227/175.1 |
| 2012/0265196 A1* | 10/2012 | Turner | A61B 18/1206 606/34 |
| 2014/0148818 A1* | 5/2014 | Komuro | A61B 34/37 606/130 |
| 2015/0209035 A1* | 7/2015 | Zemlok | A61B 17/07207 73/1.01 |
| 2015/0282862 A1* | 10/2015 | Warren | A61B 18/1206 606/34 |
| 2017/0028549 A1* | 2/2017 | Battisti | B25J 9/161 |
| 2018/0154521 A1* | 6/2018 | Bosscher | B25J 15/0066 |

* cited by examiner

SELF-IDENTIFYING SURGICAL CLAMP, FIDUCIAL ELEMENT FOR USE WITH SUCH A CLAMP AND KITS COMPRISING SUCH CLAMPS AND FIDUCIAL ELEMENTS

BACKGROUND OF THE INVENTION

Field of the Invention

The present invention relates to surgical devices, more in particular it refers to a surgical clamp for use in navigated or robotic systems.

Description of the Related Art

Computer aided surgery (CAS) systems have been developed to increase safety and reduce risks in existing surgeries and have enabled the implementation of new surgical procedures such as minimally invasive surgeries. CAS systems include navigators that guide the surgeon during the intervention such as the one presented in U.S. Pat. No. 6,351,659 B1. Navigators are usually based on an optical tracking system that continually determines the position and orientation of the patient and of some surgical instruments with respect to a fixed coordinate system. Such information is matched with a virtual representation of the anatomy of the patient in order to give visual feedback to the surgeon. The surgeon can then observe the trajectory of the surgical instruments with respect to some anatomical sites that are otherwise not visible, for instance, because they are hidden by soft tissues. Another type of CAS systems are robotic assistants based on optical or mechanical trackers. Robotic assistants such as the one described in US 2014/0350571 A1 present a physical guide to provide a trajectory for the surgical instruments to reach pre-planned anatomical sites. All these systems are based on fixing a fiducial element that is part of the tracking mechanism, on an anatomical site of the patient.

In some spine surgeries, more than one anatomical site has to be tracked during the intervention, for instance, to operate on several vertebral levels as described in Ughwanogho et al. 2010 (E. Ughwanogho, J. M. Flynn, "*Current Navigation Modalities in Spine Surgery*", University of Pennsylvania Orthopaedic Journal, vol. 20, pages 65-69, May 2010). In such interventions, a unique clamp can be used to operate the different regions sequentially by fixing the clamp on a targeted vertebra when a region is going to be intervened and releasing it to move to the next one. Another option is to fix more than one clamp at the same time on the different regions and make the system track one of them. In both cases, the surgeon has to notify the system where the tracker is mounted or which reference array is visible in order to associate the pre-surgical image of the patient with the current location of the clamp. This procedure presents some risks since a human error can make the system think that the tracker is associated with a surgical site that does not correspond to the true physical location. In such a situation, the trajectory that is presented to the surgeon with respect to the virtual representation of the patient will not correspond with the physical location with the risks that this entails. In the current art there is no system that describes an automatic identification mechanism to let the system know where a tracker is mounted.

SUMMARY OF THE INVENTION

The present invention provides a reference clamp provided with a unique identifier in the form of a passive electric circuit having a predetermined impedance value that can be automatically identified by the tracking device. In a kit comprising a plurality of clamps, the identifiers are automatically associated with the different anatomical sites at the beginning of the intervention during the patient registration process. The invention further comprises a fiducial complementary to the clamp and a kit of fiducial elements each provided with a different configuration of radiopaque spheres.

BRIEF DESCRIPTION OF THE DRAWINGS

To complete the description and provide for better understanding of the invention, a set of drawings is provided. Said drawings illustrate a preferred embodiment of the invention, which should not be interpreted as restricting the scope of the invention, but just as an example of how the invention can be carried out.

DESCRIPTION OF THE PREFERRED EMBODIMENTS

This invention presents a surgical clamp to locate and track precisely pre-planned surgical sites in the operating room. Thanks to the invention, navigated or robotically-assisted surgery is executed in a minimally invasive fashion with a high degree of accuracy. The targeted operation is the insertion of pedicle screws in vertebrae, but can also be extended to other types of surgery. The precise location of the screws might be planned before the patient goes into the operating room on a pre-surgical image of the patient or can be planned during the surgery if an intra-operative three-dimensional imaging device is available, usually a computerized tomography system (CT). Planning the surgery includes defining the size, location and orientation of pedicle screws in the targeted vertebrae.

Figure 1A:
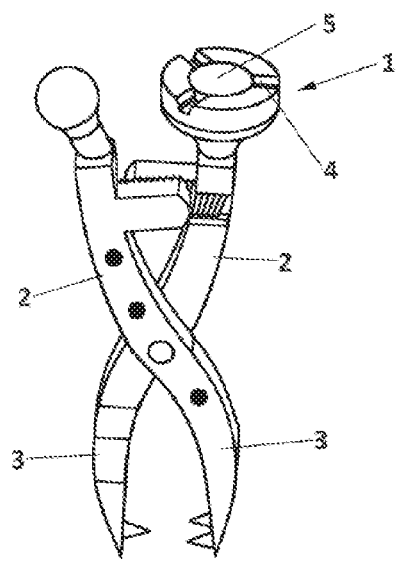
FIG. 1 shows a clamp and a registration fiducial element according to the invention.
Figure 1B:
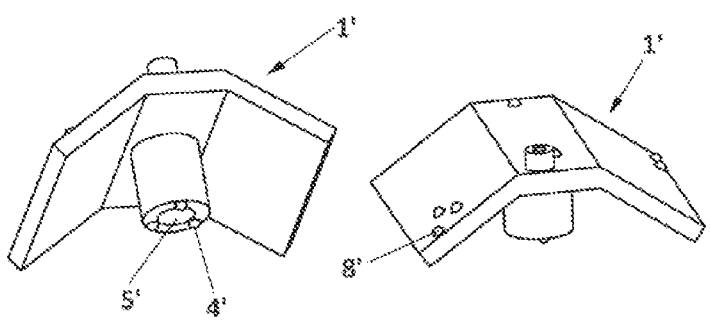
Figure 2:
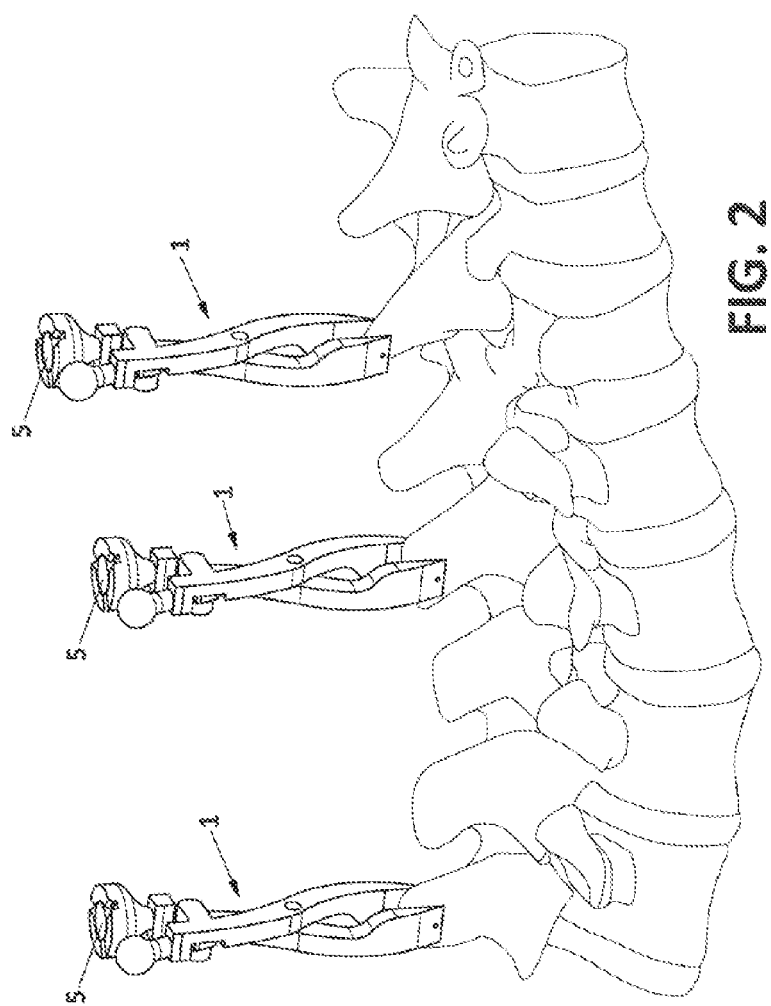
FIG. 2 shows a set of three clamps according to the invention attached to the spine of a patient.

A three-dimensional image of the anatomical site can be taken before the patient goes into the operating room. In this example, this anatomical site corresponds to a section of the spine of the patient. The surgeon plans the surgery on this preoperative image. Note that this step can be performed days before the surgery is scheduled. When the patient goes into the operating room and in order to perform the surgery with a navigation system or robotic assistant, the relative position and orientation of the tracking device with respect to the anatomical site has to be established. This is achieved by a two step process. First, the relative position and orientation of the targeted vertebrae with respect to a reference that is rigidly fixed to the bone is registered. The clamp (1) of the invention, as shown in FIG. 1, is rigidly fixed to the bone and acts as the reference. In order to complete the registration step, once the clamp is secured to the spinous process of a vertebra by means of its two jaws (3), an element with a known geometry is temporarily mounted on the clamp (1'). This element is known in the literature as registration fiducial element. When the registration step is completed the registration fiducial element is removed from the clamp. Note that the clamp is still attached to the bone. Then, the relative position and orientation of the clamp are tracked during the surgery with a mechanical or optical tracking device. A lower portion (3) of the reference clamp is rigidly fixed to the bone by means of its jaws and an upper portion (2) presents a kinematic coupling mechanism (4, 5). The kinematic coupling mechanism is prepared to receive the registration fiducial element with a variety of markers or one end of a tracking device.

Figure 3:
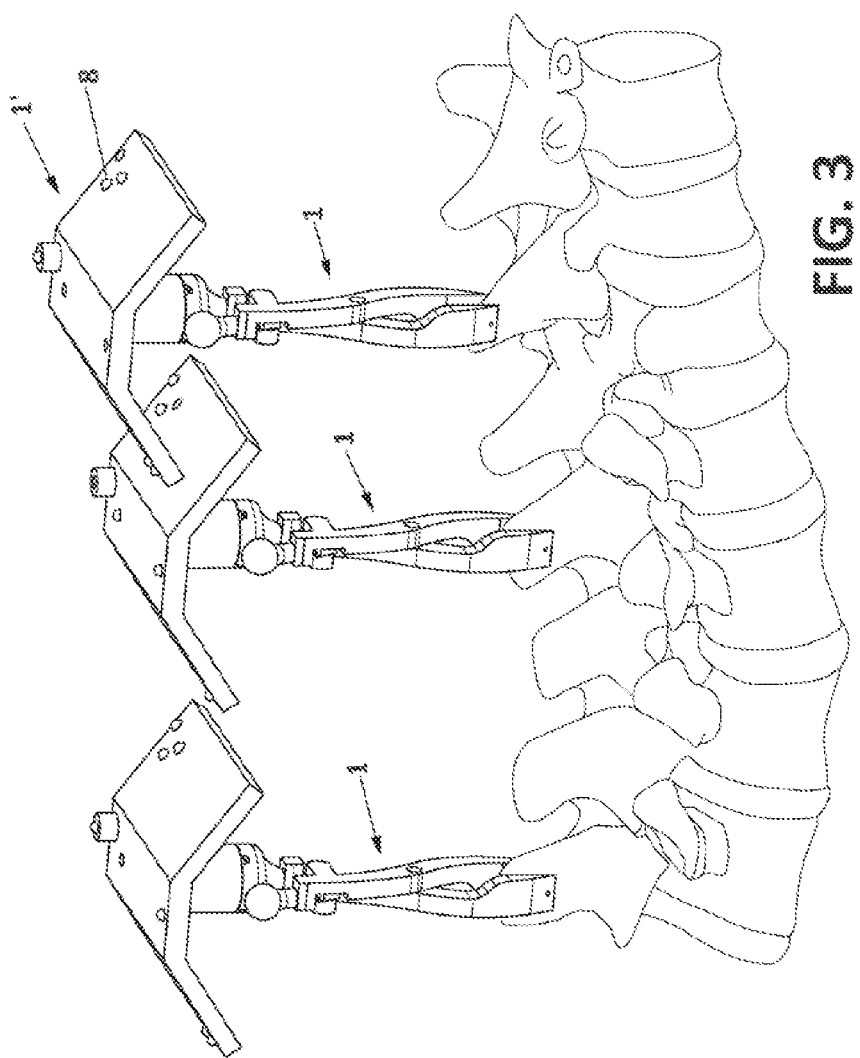
FIG. 3 shows the same three clamps with registration fiducial elements attached thereon.

With reference to FIG. 3, the registration fiducial element (1') is a rigid body made of a radiolucent material with several radiopaque spheres (8') disposed in a known geometry. The radiopaque spheres are easily identified in a two-dimensional radiograph or a three-dimensional computerized tomography since they present a high contrast with respect to the rest of the body that composes the registration fiducial element. When the reference clamp is fixed to the target bone and the registration fiducial element is mounted on the clamp, intra-operative images of the region are taken. It is desirable to use a three-dimensional intra-operative acquisition device in order to achieve higher accuracies. If such device is not available, at least two two-dimensional radiographs have to be acquired at different orientations in order to be able to precisely locate the position in space of the fiducial element from the two-dimensional projections of the spheres. In the present invention, a number of clamps with unique identifiers are available and each clamp has an associated fiducial element with a unique spheres configuration. These different configurations of the radiopaque spheres allow the unambiguous identification of the clamps during the registration procedure. Therefore, when the registration procedure is completed, the system knows exactly which clamp is fixed in the different anatomical sites where the surgery is going to be performed.

The accuracy of the registration procedure is heavily dependent on the distance between the spheres of the fiducial element and the target area. In order to increase the accuracy it is therefore desirable to place the spheres as close to the target as possible. In this embodiment, the target area is the pedicle of the vertebra, and the element of the system that is closer to this area is the reference clamp. In the present invention, the reference clamp can also include radiopaque spheres (8) at the upper portion that are used in the registration process. This makes the registration procedure more robust increasing the accuracy of the overall system and reducing the risks that are inherent to the intervention.

The registration procedure, first, establishes the exact position of the reference clamp. This can be done thanks to the fact that the radiopaque spheres are easily detected in the intra-operative images and the geometries of the reference clamp and the fiducial element are known. As mentioned before, the intra-operative images can be a three-dimensional reconstruction of the region of interest or several two-dimensional radiographs. In the case of a three-dimensional intra-operative acquisition, the location of the reference clamp is easily established by finding the radiopaque spheres in the three-dimensional volume. If registration is performed making use of two-dimensional radiographs, the position of the spheres is obtained by back-projecting their positions from the two-dimensional images and finding their position in the three-dimensional space by triangulating the various projections of each sphere.

Then, the position and orientation of the vertebra in the three-dimensional pre-operative image is matched with the intra-operative image of the vertebra. This is performed using standard intensity based registration algorithms that find the transformation that relates the two geometries. At this point, a surgical site defined on the pre-operative image of the vertebra can be identified in the operating room with respect to the reference clamp. It is important to note that the reference clamp is rigidly fixed to the bone, consequently, there is no relative movement between the clamp and the bone. Therefore, the registration fiducial element can be removed leaving the reference clamp fixed to the bone. From this point, the position and orientation of the vertebra is precisely tracked during the surgery by tracking the position and orientation of the reference clamp. The registration fiducial element can be easily removed from the reference clamp thanks to the coupling mechanism that is described next.

The coupling mechanism (FIG. 1) is based on a magnetic kinematic coupling system that comprises, advantageously but not necessarily, two portions, each portion comprising a magnet (5, 5'), the magnets being of opposite polarities so that they cooperate with each other to form the coupling. The mountable element can be a registration fiducial element or a tracker device. Preferably, three V-shaped grooves (4) on the clamp portion and three spheres (4') on the other portion (fiducial element or tracker) provide the magnet coupling together with the magnets. This coupling creates a precise and repeatable interface between the two rigid bodies. This system provides six contact points—two per sphere—in order to guarantee that the coupling mechanism constrains the six degrees of freedom (three degrees of freedom for the position and another three for the rotation) of the relative movement between the clamp and the tip of the tracker. A magnet (5, 5') in the center of each portion provides the strength required to avoid any relative movement between the clamp and the tip of the tracker by keeping both portions together. The force exerted by the magnet is such that it ensures the connection between the clamp and the tracker during the intervention. However, this force is such that the connection can be released by a human operator in order to allow the system to be easily removed at any time. The most stable kinematic coupling would be obtained when the three V-shaped grooves form angles of 120°. However, for the invention it is preferred that the three V-shaped grooves form three angles such that the coupling mechanism can only be engaged in a unique position. For instance, angles of 110°, 110° and 140° guarantee that the coupling mechanism is engaged in a unique position. For this purpose, at least one of the angles must be different from the other two.

The clamp is composed of two rigid halves, each half presenting a jaw at its lower portion (3) with spikes. The spikes of each jaw penetrate the surface of the bone in order to guarantee that the clamp is securely fixed to the bone during the intervention. The upper portion (2) of one of the halves presents the base of the kinematic coupling mechanism with the three V-shaped grooves. The other half presents a round ending at its upper portion to ease the tightening of the clamp with an auxiliary tool. This tool is adapted to tighten the present clamp. The clamp presents a ratchet teeth mechanism to allow the tightening of the clamp against the bone and prevent the clamp to be released from the bone during the intervention. The ratchet tightening mechanism presents teeth at both halves of the clamp in order to allow movement only in the tightening direction.

Figure 4:
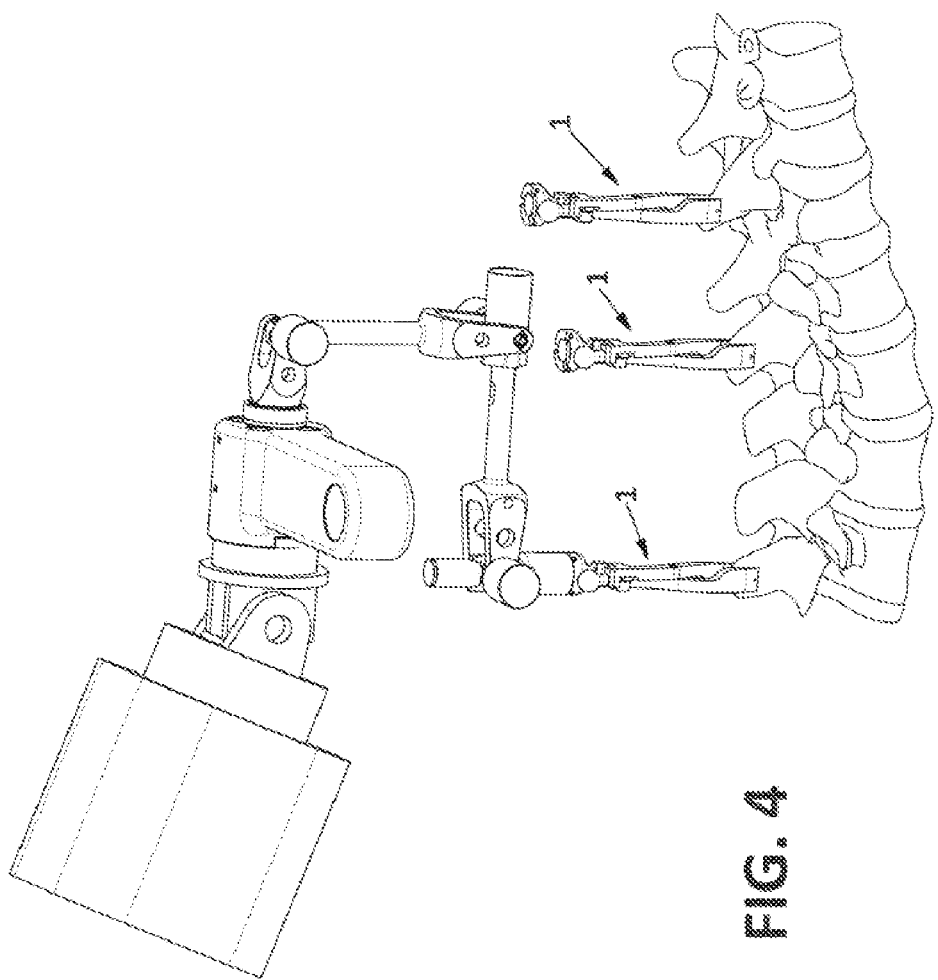
FIG. 4 shows the same three clamps with a mechanical tracker and robotic assistant mounted on one of the clamps.

The clamp and the tracker (FIG. 4) present a detection mechanism that notifies the system when the tracker is attached to the clamp. This detection mechanism is an electric circuit connected to a processing unit that is able to identify when the connection has been established. The clamp portion of the coupling mechanism, at the upper portion of the clamp, has a passive electric circuit and the tracker portion of the coupling mechanism, which is located at the tip of the latter, connects the base portion to a processing unit. The processing unit applies a small voltage, therefore, when the connection is established the electric circuit is closed and a current is detected.

Figure 5A:
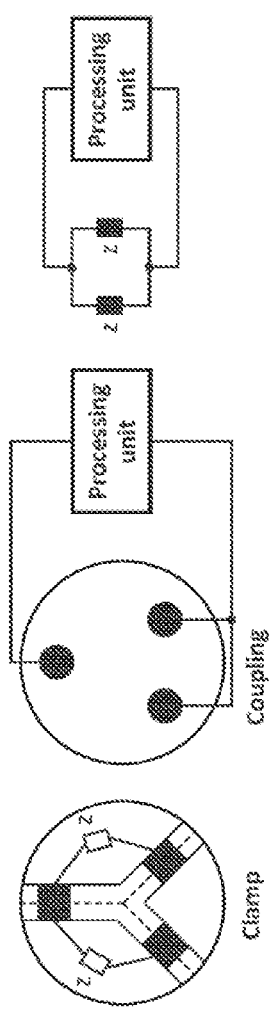
FIG. 5 shows two examples of the automatic identification electrical circuit.
Figure 5B:
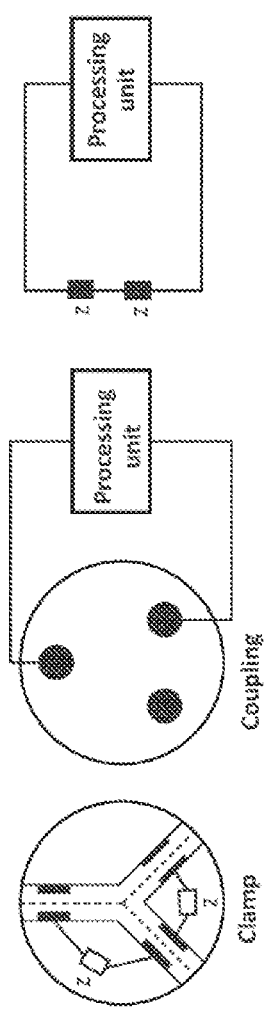

The spheres of the previously described kinematic coupling mechanism are made of an electrically conductive material and are connected to the processing unit. The V-shaped grooves present an electrically conductive section where the spheres make contact in order to establish the electrical connection between the top and base portion. FIGS. 5-a and 5-b are two examples of electric circuits that implement this detection mechanism. In both cases two impedances of value Z are used between the different contacts. In the first example, if a voltage V is applied by the processing unit the current across the circuit has a value of I=2V/Z. In the second example, if a voltage V is applied by the processing unit the current across the circuit has a value of I=V/2Z.

Other configurations of passive circuits include one or more resistances, capacitors, coils or any combination of the latter. This idea is extended in the present invention to detect automatically different clamps. The number of vertebrae that have to be intervened depend on the type of surgery and can go from only two to more than ten. In this context, the surgeon can fix several clamps at different vertebrae in order to have robust references at different locations. The robotic system will then indicate the trajectory of the screws that have to be inserted at each vertebra. In order to achieve this, it is crucial that the system is always aware of the vertebra where the tracker is fixed since the trajectories of the screws are different from vertebra to vertebra. To make the system detect automatically the different clamps, each clamp presents a different impedance Z in the detection circuit. The processing unit can therefore identify to which clamp the tracker is connected to by measuring the current that is circulating across the clamp. The different clamps have an identifier associated to it.

Clamps with different identifiers have different registration fiducial elements associated to them in order to identify the clamps during the registration procedure as well. The different registration fiducial elements present the same body of radiolucent material but the configuration of the radiopaque spheres is different. The different configurations of the spheres make it possible to identify the clamp during the registration step and therefore identify which clamp is fixed to which vertebra. The system can thus associate a vertebra to a clamp identifier and when the tracker is connected to a clamp the system can immediately identify in which vertebra the tracker is mounted.

The clamp is rigidly fixed to the bone during the intervention and as a consequence it has to be made of a material that is stiff and biocompatible. Titanium is the metal of choice in many medical applications since it satisfies both properties. Titanium alloy Ti6Al4V is commonly used for prosthetics or instrumentation and therefore is the preferred material for the clamp. Stainless steel is also suitable for such applications.

Alternatively the clamp can be made of carbon fiber reinforced ceramic material that has the advantage of being radiolucent.

The invention claimed is:

1. A surgical clamp comprising two halves, each half with an upper and a lower portion, the lower portion of one half and the lower portion of the other half forming two jaws adapted to be in contact with a surgical site, wherein one of the upper portions comprises:
    a first portion of kinematic coupler configured to be coupled with a second portion of kinematic coupler of a registration fiducial element or a tracking device; and
    a passive circuit with a predetermined impedance value, the passive circuit being configured to connect with the tracking device when the tracking device is coupled to the first portion of kinematic coupler of the surgical clamp,
    wherein the first portion of kinematic coupler comprises a first impedance between a first V-shaped groove and a second V-shaped groove, and a second impedance between the first V-shaped groove and a third V-shaped groove, the value of the second impedance being equal to the value of the first impedance, wherein each of the first, second and third V-shaped grooves comprises a conductive section,
    wherein when the surgical clamp, in operating mode, is coupled to the tracking device, an electrical connection between the passive circuit and the tracking device is configured so that the passive circuit is provided between the first V-shaped groove and a connection between the second V-shaped groove and the third V-shaped groove in such a way that the first impedance and the second impedance are in parallel,
    wherein the second portion of kinematic coupler is configured such that the electrical connection with the passive circuit is formed by connecting a first terminal with a first sphere adapted to contact to the conductive section of the first V-shaped groove and connecting a second terminal with a second sphere and a third sphere, the second and third spheres being in electrical communication, the second sphere adapted to contact the conductive section of the second V-shaped groove and the third sphere adapted to contact the conductive section of the third V-shaped groove.

2. The surgical clamp of claim 1, wherein the first portion of kinematic coupler comprises a first magnet, and the first, second and third V-shaped grooves being arranged around the first magnet forming three angles.

3. The clamp of claim 1 further comprising radiopaque spheres at the upper portion.

4. A surgical clamp comprising two halves, each half with an upper and a lower portion, the lower portion of one half and the lower portion of the other half forming two jaws adapted to be in contact with a surgical site, wherein one of the upper portions comprises:
    a first portion of kinematic coupler configured to be coupled with a second portion of kinematic coupler of a registration fiducial element or a tracking device; and
    a passive circuit with a predetermined impedance value, the passive circuit being configured to connect with the tracking device when the tracking device is coupled to the first portion of kinematic coupler of the surgical clamp,
    wherein the first portion of kinematic coupler comprises a first impedance between a first V-shaped groove and a second V-shaped groove, and a second impedance between the second V-shaped groove and a third V-shaped groove, the value of the second impedance being equal to the value of the first impedance;
    wherein each of the first, second and third V-shaped grooves comprises a conductive section, each conductive section comprising a first conductive part for a contact point and a second conductive part for a further contact point separated from the first conductive part; and wherein when the surgical clamp, in operating mode, is coupled to the tracking device, an electrical connection between the passive circuit and the tracking device is configured so that the passive circuit is provided between the first V-shaped groove and a connection between the second V-shaped groove and the third V-shaped groove in such a way that the first impedance and the second impedance are in series;

wherein the second portion of kinematic coupler is configured such that the electrical connection with the passive circuit is formed by connecting a first terminal with a first sphere adapted to contact to the conductive section of the first V-shaped groove and connecting a second terminal with a third sphere, a second sphere adapted to contact the conductive section of the second V-shaped groove and the third sphere adapted to contact the conductive section of the third V-shaped groove.

5. The surgical clamp of claim 2, wherein one of the angles is different from the other two.

6. A kit comprising a plurality of surgical clamps of claim 1, wherein the passive circuit of each surgical clamp has a different impedance.

7. A registration fiducial element for use with the surgical clamp of claim 1, comprising radiolucent material, wherein the second portion of kinematic coupler is configured to be coupled with the first portion of kinematic coupler of the surgical clamp.

8. The registration fiducial element of claim 7 further comprising a predetermined configuration of radiopaque spheres at a top portion.

9. A kit comprising a plurality of registration fiducial elements of claim 7, wherein each registration fiducial element comprises a different configuration of radiopaque spheres.

10. A kit comprising a plurality of registration fiducial elements of claim 8, wherein each registration fiducial element comprises a different configuration of radiopaque spheres.

11. A registration fiducial element for use with the surgical clamp of claim 2, comprising radiolucent material, wherein the second portion of kinematic coupler is configured to be coupled with the first portion of kinematic coupler of the surgical clamp.

12. The registration fiducial element of claim 11 further comprising a predetermined configuration of radiopaque spheres at a top portion.

13. A kit comprising a plurality of registration fiducial elements of claim 11, wherein each registration fiducial element comprises a different configuration of radiopaque spheres.

14. A kit comprising a plurality of registration fiducial elements of claim 12, wherein each registration fiducial element comprises a different configuration of radiopaque spheres.

15. The surgical clamp of claim 4, further comprising radiopaque spheres at the upper portion.

16. The surgical clamp of claim 1, wherein the first, second and third V-shaped grooves being arranged forming three angles, and one of the angles is different from the other two.

17. The surgical clamp of claim 4, wherein the first, second and third V-shaped grooves being arranged forming three angles, and one of the angles is different from the other two.

18. The surgical clamp of claim 4, wherein the first portion of kinematic coupler comprises a first magnet, and the first, second and third V-shaped grooves being arranged around the first magnet forming three angles.

19. The surgical clamp of claim 18, wherein one of the angles is different from the other two.

20. A kit comprising a plurality of surgical clamps of claim 4, wherein the passive circuit of each surgical clamp has a different impedance.

* * * * *